US010314793B2

(12) United States Patent
Fantuzzi

(10) Patent No.: US 10,314,793 B2
(45) Date of Patent: *Jun. 11, 2019

(54) SOLUBILIZED COQ-10

(71) Applicant: Soft Gel Technologies, Inc., Los Angeles, CA (US)

(72) Inventor: Michael Fantuzzi, Yichang (CN)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/229,624

(22) Filed: Aug. 5, 2016

(65) Prior Publication Data

US 2017/0119696 A1 May 4, 2017

Related U.S. Application Data

(63) Continuation of application No. 14/560,136, filed on Dec. 4, 2014, now abandoned, which is a continuation of application No. 14/165,319, filed on Jan. 27, 2014, now Pat. No. 8,932,585, which is a continuation of application No. 13/357,402, filed on Jan. 24, 2012, now Pat. No. 8,658,161, which is a continuation of application No. 10/953,328, filed on Sep. 29, 2004, now Pat. No. 8,105,583, which is a continuation-in-part of application No. 10/674,268, filed on Sep. 29, 2003, now Pat. No. 8,124,072.

(51) Int. Cl.
| | | |
|---|---|---|
| *A61K 31/122* | (2006.01) | |
| *A61K 9/48* | (2006.01) | |
| *A61K 31/045* | (2006.01) | |
| *A61K 31/12* | (2006.01) | |
| *A61K 47/06* | (2006.01) | |
| *A23L 33/16* | (2016.01) | |
| *A61K 47/44* | (2017.01) | |

(52) U.S. Cl.
CPC ............ *A61K 31/122* (2013.01); *A23L 33/16* (2016.08); *A61K 9/4825* (2013.01); *A61K 9/4858* (2013.01); *A61K 9/4875* (2013.01); *A61K 31/045* (2013.01); *A61K 31/12* (2013.01); *A61K 47/06* (2013.01); *A61K 47/44* (2013.01)

(58) Field of Classification Search
CPC .................................................. A61K 31/122
See application file for complete search history.

(56) References Cited

U.S. PATENT DOCUMENTS

| | | |
|---|---|---|
| 4,029,760 A | 6/1977 | De Roeck born Holtzhauer |
| 4,343,816 A | 8/1982 | Cavazza |
| 4,559,222 A | 12/1985 | Enscore et al. |
| 4,565,700 A | 1/1986 | Suzuki |
| 4,599,232 A | 7/1986 | Bertelli |
| 4,687,782 A | 8/1987 | Brantman |
| 4,824,669 A | 4/1989 | Folkers et al. |
| 4,840,970 A | 6/1989 | Ohasi et al. |
| 5,030,458 A | 7/1991 | Shug et al. |
| 5,240,961 A | 8/1993 | Shug |
| 5,290,605 A | 3/1994 | Shapira |
| 5,298,246 A | 3/1994 | Yano et al. |
| 5,310,578 A | 5/1994 | Thurn-Muller et al. |
| 5,362,753 A | 11/1994 | Blum et al. |
| 5,378,461 A | 1/1995 | Neigut |
| 5,391,550 A | 2/1995 | Carniglia et al. |
| 5,431,916 A | 7/1995 | White |
| 5,500,416 A | 3/1996 | Miyazawa et al. |
| 5,504,072 A | 4/1996 | Schmidl et al. |
| 5,512,691 A | 4/1996 | Barnicki et al. |
| 5,532,002 A | 7/1996 | Story |
| 5,552,167 A | 9/1996 | Taylor et al. |
| 5,560,928 A | 10/1996 | Defelice |
| 5,591,772 A | 1/1997 | Lane et al. |
| 5,626,849 A | 5/1997 | Hastings et al. |
| 5,637,316 A | 6/1997 | Ribier et al. |
| 5,645,856 A | 7/1997 | Lacey et al. |
| 5,670,320 A | 9/1997 | Wallace et al. |
| 5,686,491 A | 11/1997 | Sherwood |
| 5,716,928 A | 2/1998 | Benet et al. |
| 5,756,291 A | 5/1998 | Griffin |
| 5,843,476 A | 12/1998 | Ribier et al. |
| 5,858,401 A | 1/1999 | Bhalani et al. |
| 5,889,062 A | 3/1999 | Hoppe et al. |
| 5,891,469 A | 4/1999 | Amselem |
| 5,912,272 A | 6/1999 | Hoppe et al. |
| 5,916,591 A | 6/1999 | Biedel-Willkommen |
| 5,948,443 A | 9/1999 | Riley et al. |
| 5,968,987 A | 10/1999 | Charman et al. |
| 5,976,568 A | 11/1999 | Riley |

(Continued)

FOREIGN PATENT DOCUMENTS

| | | |
|---|---|---|
| DE | 3512054 | 10/1986 |
| EP | 0882450 | 1/1998 |

(Continued)

OTHER PUBLICATIONS

English translation of Furointo Sangyo KK, JP S57-042616, 1982.*
Lota et al., "Volatile components of peel and leaf oils of lemon and lime species," J Agric Food Chem 50:796-805, 2002.*
Anderson Provisional U.S. Appl. No. 60/253,874, David M. Anderson, Applicant, filed Nov. 29, 2000, 21 pages.
Al-Hasso, Shahla, "Coenzyme Q10: A Review," Hospital Pharmacy, vol. 36, No. 1, pp. 51-55, 2000 Facts and Comparisons.
Author Unknown, "pformulate: A Soft Gell!!" 2000, pp. 1-6, found at URL: http://www.pformulate.com/pformsoftgel.htm.
Author Unknown, Paul Karrer Biography, Nobel Prizes, Nobel Prize in Chemistry, nobelprize.org, printed on Jan. 5, 2007, 2 pages.
Author Unknown, Oilseeds International Ltd., Rice bran oil—a health benefit, http://www.oilseedssf.com/products/prod.rice.html, 2002, printed on Mar. 6, 2006; 2 pages.

(Continued)

*Primary Examiner* — Rosanne Kosson
(74) *Attorney, Agent, or Firm* — Padda Law Group

(57) ABSTRACT

The present invention is directed to compositions and methods of delivery of CoQ-10 solubilized in monoterpenes. Use of monoterpenes as dissolving agents, greatly effects the ability to incorporate greater amounts of bioactive CoQ-10 in formulations, such as soft gel capsules.

19 Claims, 2 Drawing Sheets

(56) References Cited

U.S. PATENT DOCUMENTS

| | | |
|---|---|---|
| 5,977,162 A | 11/1999 | Seidman |
| 5,980,939 A | 11/1999 | Kim et al. |
| 5,985,344 A | 11/1999 | Cherukuri et al. |
| 6,008,192 A | 12/1999 | Al-Razzak et al. |
| 6,020,383 A | 2/2000 | Stone et al. |
| 6,033,678 A | 3/2000 | Lorenzen |
| 6,048,846 A | 4/2000 | Cochran |
| 6,048,886 A | 4/2000 | Neigut |
| 6,054,136 A | 4/2000 | Farah et al. |
| 6,056,971 A | 5/2000 | Goldman |
| 6,063,432 A | 5/2000 | Maxell et al. |
| 6,069,167 A | 5/2000 | Sokol |
| 6,080,788 A | 6/2000 | Sole et al. |
| 6,096,338 A | 8/2000 | Lacy et al. |
| 6,121,234 A | 9/2000 | Benet et al. |
| 6,174,547 B1 | 1/2001 | Dong et al. |
| 6,184,255 B1 | 2/2001 | Mae et al. |
| 6,197,349 B1 | 3/2001 | Westesen et al. |
| 6,200,550 B1 | 3/2001 | Masterson et al. |
| 6,203,818 B1 | 3/2001 | Vester |
| 6,207,137 B1 | 3/2001 | Shuch et al. |
| 6,218,436 B1 | 4/2001 | Howard et al. |
| 6,232,346 B1 | 5/2001 | Sole et al. |
| 6,261,575 B1 | 7/2001 | Hoppe et al. |
| 6,267,985 B1 | 7/2001 | Chen et al. |
| 6,277,431 B1 | 8/2001 | Berry et al. |
| 6,284,268 B1 | 9/2001 | Mishra et al. |
| 6,300,361 B1 | 10/2001 | Vivilecchia et al. |
| 6,300,377 B1 | 10/2001 | Chopra |
| 6,335,361 B1 | 1/2002 | Hamilton |
| 6,342,526 B1 | 1/2002 | Vervuert et al. |
| 6,365,181 B1 | 4/2002 | Matthews |
| 6,368,618 B1 | 4/2002 | Jun et al. |
| 6,426,362 B1 | 7/2002 | Miller et al. |
| 6,428,779 B1 | 8/2002 | Sauermann et al. |
| 6,436,431 B1 | 8/2002 | Hoffpauer et al. |
| 6,441,050 B1 | 8/2002 | Chopra |
| 6,455,589 B1 | 9/2002 | Ames et al. |
| 6,469,024 B2 | 10/2002 | Tino et al. |
| 6,472,378 B2 | 10/2002 | von Borstel |
| 6,479,069 B1 | 11/2002 | Hamilton |
| 6,503,483 B2 | 1/2003 | Shuch et al. |
| 6,503,506 B1 | 1/2003 | Germano |
| 6,503,523 B2 | 1/2003 | Hoppe et al. |
| 6,506,915 B1 | 1/2003 | West |
| 6,528,042 B1 | 3/2003 | Brown et al. |
| 6,545,184 B1 | 4/2003 | Lipshutz |
| 6,552,004 B1 | 4/2003 | Elazhary et al. |
| 6,562,869 B1 | 5/2003 | Hamilton et al. |
| 6,569,463 B2 | 5/2003 | Patel et al. |
| 6,579,854 B1 | 6/2003 | Mitchell et al. |
| 6,616,942 B1 | 9/2003 | Udell |
| 6,623,734 B2 | 9/2003 | Udell et al. |
| 6,630,170 B2 | 10/2003 | Balkus et al. |
| 6,664,287 B2 | 12/2003 | Avery et al. |
| 6,730,319 B2 | 5/2004 | Maeder et al. |
| 6,740,338 B1 | 5/2004 | Chopra |
| 6,782,307 B2 | 8/2004 | Wilmott et al. |
| 6,790,465 B2 | 9/2004 | Weissman |
| 6,806,259 B2 | 10/2004 | Udell et al. |
| 6,855,733 B2 | 2/2005 | Udell et al. |
| 6,955,820 B1 | 10/2005 | Udell |
| 7,015,245 B2 | 3/2006 | Rich et al. |
| 7,026,361 B2 | 4/2006 | Minemura et al. |
| 7,060,263 B2 | 6/2006 | Udell et al. |
| 7,169,385 B2 | 1/2007 | Fantuzzi et al. |
| 7,182,950 B2 | 2/2007 | Garti et al. |
| 7,220,429 B2 | 5/2007 | Udell |
| 7,273,606 B2 | 9/2007 | Fantuzzi et al. |
| 7,273,622 B2 | 9/2007 | Udell et al. |
| 7,588,786 B2 | 9/2009 | Khan et al. |
| 7,713,523 B2 | 5/2010 | Fantuzzi et al. |
| 7,815,943 B2 | 10/2010 | Hennen |
| 8,097,279 B2 | 1/2012 | Hassan et al. |
| 8,105,583 B2 * | 1/2012 | Fantuzzi ............ A61K 31/122 424/455 |
| 8,124,072 B2 * | 2/2012 | Fantuzzi ............ A61K 9/4858 424/452 |
| 8,147,826 B2 | 4/2012 | Fantuzzi |
| 8,343,541 B2 | 1/2013 | Fantuzzi |
| 8,506,859 B2 | 8/2013 | Fantuzzi |
| 8,506,995 B2 | 8/2013 | Udell |
| 8,617,541 B2 * | 12/2013 | Fantuzzi ............ A61K 9/4858 424/455 |
| 8,658,161 B2 * | 2/2014 | Fantuzzi ............ A61K 31/122 424/456 |
| 8,865,032 B2 | 10/2014 | Fantuzzi |
| 8,932,584 B2 * | 1/2015 | Fantuzzi ............ A61K 9/4858 424/456 |
| 8,932,585 B2 * | 1/2015 | Fantuzzi ............ A61K 31/122 424/456 |
| 2002/0048798 A1 | 4/2002 | Avery et al. |
| 2002/0098172 A1 | 7/2002 | Udell et al. |
| 2003/0044474 A1 | 3/2003 | Tao |
| 2003/0082168 A1 | 5/2003 | Yegorova |
| 2003/0108600 A1 | 6/2003 | Okibayahi et al. |
| 2003/0119781 A1 | 6/2003 | Udell et al. |
| 2003/0147927 A1 | 8/2003 | Khan et al. |
| 2003/0176500 A1 | 9/2003 | Molly et al. |
| 2003/0232076 A1 | 12/2003 | Makino et al. |
| 2003/0232095 A1 | 12/2003 | Garti et al. |
| 2004/0001874 A1 | 1/2004 | Davidson et al. |
| 2004/0047922 A1 | 3/2004 | Elstner |
| 2004/0106674 A1 | 6/2004 | Rich et al. |
| 2004/0126432 A1 | 7/2004 | Hennen |
| 2004/0166157 A1 | 8/2004 | Thombre |
| 2005/0025756 A1 | 2/2005 | Erwin |
| 2005/0031681 A1 | 2/2005 | Udell et al. |
| 2005/0036998 A1 | 2/2005 | Udell et al. |
| 2005/0037066 A1 | 2/2005 | Udell et al. |
| 2005/0069582 A1 | 3/2005 | Fantuzzi |
| 2005/0070611 A1 | 3/2005 | Fantuzzi |
| 2005/0169983 A1 | 8/2005 | Hassan et al. |
| 2006/0013888 A1 | 1/2006 | Fantuzzi et al. |
| 2007/0269508 A1 | 11/2007 | Udell |
| 2008/0003279 A1 | 1/2008 | Udell |
| 2008/0020022 A1 | 1/2008 | Udell |
| 2008/0089877 A1 | 4/2008 | Udell et al. |
| 2008/0152707 A1 | 6/2008 | Fantuzzi et al. |
| 2008/0226710 A1 | 9/2008 | Fantuzzi |
| 2012/0121566 A1 | 5/2012 | Fantuzzi |
| 2012/0128769 A1 | 5/2012 | Fantuzzi |
| 2012/0153519 A1 | 6/2012 | Fantuzzi |
| 2013/0129821 A1 | 5/2013 | Fantuzzi |

FOREIGN PATENT DOCUMENTS

| | | |
|---|---|---|
| EP | 0888774 | 1/1999 |
| EP | 1728506 | 3/2006 |
| JP | 55081813 | 6/1980 |
| JP | S57042616 | 3/1982 |
| JP | 5770815 | 5/1982 |
| JP | S57142911 | 9/1982 |
| JP | 59172417 | 9/1984 |
| WO | 88003015 | 5/1988 |
| WO | 98040086 | 9/1998 |
| WO | 98056368 | 12/1998 |
| WO | 00051574 | 9/2000 |
| WO | 01052822 | 7/2001 |
| WO | 02009685 | 2/2002 |
| WO | 03105607 | 12/2003 |
| WO | 04066925 | 8/2004 |
| WO | 05032278 | 4/2005 |
| WO | 05089740 | 9/2005 |
| WO | 05092123 | 10/2005 |

OTHER PUBLICATIONS

Bhandari, et al., "Preparation, Characterization and Evaluation of Coenzyme Q10 Binary Solid Dispersions for Enhanced Solubility and Dissolution," Biol Pharm. Bull., 2007, vol. 30, No. 6, pp. 1171-1176.

(56) References Cited

OTHER PUBLICATIONS

Bliznakov, et al., "Biochemical and Clinical Consequencs of Inhibiting Coenzyme Q10 Biosynthesis by Lipid-Lowering HMG-CoA Reductase Inhibitors (Statins): A Critical Overview," Advances in Therapy, Jul./Aug. 1998, vol. 15, No. 4, pp. 218-222.
Chopra, et al., "Relative Bioavailability of Coenzyme Q10 Formulations in Human Subjects," Internat. J. Vit. Nutr. Res., 1998, vol. 68, pp. 109-113.
Chopra, et al., "A New Coenzyme Q10 Preparation with Enhanced Bioavailability," FASEB Journal, 1997, vol. 11, No. 3, pp. A586 (Abstract).
COMAX Q10 Trademark Registration Abstract and Specimen, Registration No. 1764014, registered Apr. 13, 1993, 26 pages.
Constantinescu, et al., "A Randomized Study of the Bioavailability of Different Formulations of Coenzyme Q10 (Ubiquinon)," The Journal of Clinical Pharmacology, 2007; 47: 1580-1586.
CRC Handbook of Chemistry and Physics, 51st Edition, R.C. Weast (Editor), The Chemical Rubber Co., Cleveland, Ohio, 1970, pp. C-309, 356, 364, 392, 434 and 488.
Density of Cooking Oil, The Physics Factbook, edited by Glenn Elert, dated unknown, 3 pages.
Dictionary.com accessed on Jan. 17, 2007, "thixotropic" 1 page
Grant & Hackh's Chemical Dictionary, Definition of Gelatin, Fifth Edition, McGraw-Hill Book Company, 1987, p. 258.
Grant & Hackh's Chemical Dictionary, Definition of Gelatin, Fifth Edition, McGraw-Hill Book Company, 1987, p. 258.
Greenberg, et al., "Co-enzyme Q10: a new drug for cardiovascular disease," The Journal of Clinical Pharmacology, 1990, vol. 30, pp. 596-608.
Kang et al., "Physicochemical studies of lidocaine-menthol binary systems for enhanced membrane transport," International Journal of Pharmaceutics, 206 (2000) 35-42.
Kaplun-Frischoff, et al., "Testosterone Skin Permeation Enhancement by Menthol through Formation of Eutectic with Drug and Interaction with Skin Lipids," Journal of Pharmaceutical Sciences, vol. 86, No. 12, Dec. 1997, pp. 1394-1399.
Kommuru, et al. "A simplified chromatographic method for quantitiative determination of coenzyme Q10 in dog plasma", Journal of Pharmaceutical and Biomedical Analysis, 16 (1998) 1037-1040.
Kommuru, et al., "Racemate and Enantiomers of Ketoprofen: Phase Diagram, Thermodynamic Studies, Skin Permeability, and Use of Chiral Permeation Enhancers," Journal of Pharmaceutical Sciences vol. 87, No. 7, Jul. 1998, pp. 833-840.
Kommuru, et al., "Self-emulsifying drug delivery systems (SEDDS) of coenzyme Q10: formulation development and bioavailabiilty assessment," International Journal of Pharmaceutics, 2001, vol. 212, pp. 233-246.
Kommuru, et al., "Stability and Bioequivalence Studies of Two Marketed Formulations of Coenzyme Q10 in Beagle Dogs," Chem. Pharm. Bull. 47(7) 1024-1028 (1999).
Merriam-Webster Dictionary on Line, definition of "elixir," http://www.merriamwebster.com/dictionary/elixir, printed from the Jun. 3, 2009, 2 pages.
Nazzal et al., "Preparation and in vitro characterization of a eutectic based semisolid self-nanoemulsified drug delivery system (SNEDDS) of ubiquinone: mechanism and progress of emulsion formation," International Journal of Pharmaceutics 235 (2002) 247-265.
Nazzal et al., "Response Surface Methodology for the Optimization of Ubiquinone Self-Nonoemulsified Drug Delivery System," AAPSPharmSciTech 2002; 3 (1) article 3, pp. 1-9, Published: Feb. 8, 2002, found at URL: http://www.aapspharmscitech.org.
Padilla-Zakour, "Chemical Food Preservatives: Bonzoate and sorbate," Venture, New York State Agriculture Experimental Station, 1998, vol. 1, No. 2, 3 pages, found at URL: http://www.nysaes.cornell.edu/necfe/pubs/pdfNenture/ventureLphemical.html.
Palamakula, et al., "Preparation and In Vitro Characterization of Self-Nanoemulsified Drug Delivery Systems of Coenzyme Q10 Using Chiral Essential Oil Components," Pharmaceutical Technology, Oct. 2004, pp. 74-88.
Pouton, Colin W., "Lipid formulations for oral administration of drugs: nonemulsifying, self-emulsifying and 'self-microemulsifying' drug delivery systems," European Journal of Pharmaceutical Sciences 11 Suppl. 2 (2000) S93-S98.
RITO Partnership, Rice Bran Oil Info, http://web.archive.org/web/20020809203831/http://www.ricebranoil.info/why/index.html, web page of Aug. 9, 2002, printed from the Internet on Apr. 29, 2009, 1 page.
Shojaei et al., "Transbuccal permeation of a nucleoside analog, dideoxycytidine: effects of menthol as a permeation enhancer," International Journal of Pharmaceutics 192 (1999) 139-146.
Shrestha et al., "Aqueous Phase Behavior of Diglycerol Fatty Acid Esters," Journal of Dispersion Science and Technology, 28: pp. 883-891, 2007.
Siekmann et al., "Preparation and Physicochemical Characterization of Aqueous Dispersions of Coenzyme Q10 Nanoparticles," Pharmaceutical Research, vol. 12, No. 2, 1995.
Walker, "Mass, Weight, Density or Specific Gravity of Liquids, Specific Gravity of Liquids," 2007, Slmetric.co.uk [http://www.simetric.co.uk/si_liquids.htm], 5 pages.
Weber, et al., "Intestinal Absorption of Coenzyme Q10 Administered in a Meal or as Capsules to Healthy Subjects," Nutrition Research, vol. 17, No. 6, pp. 941-945, 1997.
Weis, et al., "Bioavailability of Four Oral Coenzyme Q10 Formulations in Health Volunteers," Molec. Aspects. Med., 1994, vol. 15, Supplement, pp. s273-s280.
Inter Partes Reexamination Proceeding for U.S. Pat. No. 8,124,072, brought by Jarrow Formulas, Inc., Sep. 15, 2012, 525 pages.
Inter Partes Reexamination Proceeding for U.S. Pat. No. 8,105,583, brought by Jarrow Formulas, Inc., Sep. 15, 2012, 557 pages.
Inter Partes Reexamination Proceeding for U.S. Pat. No. 8,147,826, brought by Jarrow Formulas, Inc., Sep. 15, 2012, 556 pages.
Office Action dated Nov. 23, 2012, U.S. Appl. No. 95/002,396, 39 pages.
Office Action dated Nov. 23, 2012, U.S. Appl. No. 95/002,405, 37 pages.
Office Action dated Nov. 23, 2012, U.S. Appl. No. 95/002,411, 38 pages.
Amendment and Response to Office Action filed Jan. 23, 2013 and refiled on May 10, 2013, U.S. Appl. No. 95/002,396, 126 pages.
Amendment and Response to Office Action filed Jan. 23, 2013, U.S. Appl. No. 95/002,405, 117 pages.
Amendment and Response to Office Action filed Jan. 23, 2013, U.S. Appl. No. 95/002,411, 68 pages.
Third Party Requestor's Comments under 35 C.F.R. 314(B)(2) and 37 C.F.R. 1.947 in Inter Partes Reexamination of U.S. Pat. No. 8,124,072, Feb. 22, 2013, 74 pages [Note: this was expunged and refiled Jun. 10, 2013].
Third Party Requestor's Comments on Patent Owner's Amendment filed May 10, 2013, Inter Partes Reexamination of U.S. Pat. No. 8,124,072, Jun. 10, 2013, 52 pages.
Third Party Requestor's Comments under 35 C.F.R. 314(B)(2) and 37 C.F.R. 1.947 in Inter Partes Reexamination of U.S. Pat. No. 8,105,583, Feb. 22, 2013, 52 pages.
Third Party Requestor's Comments under 35 C.F.R. 314(B)(2) and 37 C.F.R. 1.947 in Inter Partes Reexamination of U.S. Pat. No. 8,147,826, Feb. 22, 2013, 33 pages.
Action Closing Prosecution dated Jul. 8, 2013, U.S. Appl. No. 95/002,396, 45 pages.
Action Closing Prosecution dated Jul. 3, 2013, U.S. Appl. No. 95/002,405, 38 pages.
Action Closing Prosecution dated Jul. 3, 2013, U.S. Appl. No. 95/002,411, 35 pages.
Petition for Withdrawal of Action Closing Prosecution and Requesting Prosecution be Reopened and Comments Pursuant to Action Closing Prosecution, U.S. Appl. No. 95/002,396, filed Aug. 8, 2013, 79 pages.
Petition for Withdrawal of Action Closing Prosecution and Requesting Prosecution be Reopened and Comments Pursuant to Action Closing Prosecution, U.S. Appl. No. 95/002,405, filed Aug. 5, 2013, 79 pages.

(56) References Cited

OTHER PUBLICATIONS

Petition for Withdrawal of Action Closing Prosecution and Requesting Prosecution be Reopened and Comments Pursuant to Action Closing Prosecution, U.S. Appl. No. 95/002,411, filed Aug. 5, 2013, 79 pages.
Amendment filed Jan. 15, 2008, to Office Action dated Sep. 17, 2007, U.S. Appl. No. 10/293,932, 16 pages.
Amendment filed Mar. 11, 2009, to Office Action dated Sep. 11, 2008, U.S. Appl. No. 10/293,932, 16 pages.
Office Action dated Jul. 11, 2013, U.S. Appl. No. 13/357,402, 10 pages.
Office Action dated Aug. 21, 2012, U.S. Appl. No. 13/406,794, 8 pages.
Amendment and Response to Office Action dated Nov. 21, 2012, U.S. Appl. No. 13/406,794, 9 pages.
Final Office Action dated Dec. 14, 2012, U.S. Appl. No. 13/406,794, 7 pages.
Amendment and Response to Final Office Action dated Mar. 14, 2013, U.S. Appl. No. 13/406,794, 8 pages.
Advisory Action dated Mar. 28, 2013, U.S. Appl. No. 13/406,794, 3 pages.
Notice of Allowance and Fee(s) Due dated Jun. 25, 2013, U.S. Appl. No. 13/406,794, 6 pages.
Office Action (Restriction Requirement) dated Jan. 7, 2005, U.S. Appl. No. 10/674,268, 9 pages.
Response to Restriction Requirement dated Feb. 7, 2005, U.S. Appl. No. 10/674,268, 2 pages.
Office Action dated Mar. 11, 2005, U.S. Appl. No. 10/674,268, 8 pages.
Amendment and Response under 37 C.F.R. 1.111 dated Jun. 7, 2005, U.S. Appl. No. 10/674,268, 10 pages.
Office Action (Restriction Requirement) dated Jun. 28, 2005, U.S. Appl. No. 10/674,268, 7 pages.
Response to Restriction Requirement dated Jul. 27, 2005, U.S. Appl. No. 10/674,268, 10 pages.
Notice of Allowance and Fee(s) Due dated Aug. 26, 2005, U.S. Appl. No. 10/674,268, 11 pages.
Request for Continued Examination dated Sep. 15, 2005, U.S. Appl. No. 10/674,268, 1 page.
Declaration Under 37 C.F.R. 1.131 Antedating a Reference, dated Sep. 15, 2005, U.S. Appl. No. 10/674,268, 2 pages.
Office Action dated Sep. 30, 2005, U.S. Appl. No. 10/674,268, 8 pages.
Amendment and Response dated Dec. 20, 2005, U.S. Appl. No. 10/674,268, 13 pages.
Final Office Action dated Jan. 31, 2006, U.S. Appl. No. 10/674,268, 7 pages.
Response to Office Action Made Final, dated Apr. 28, 2006, U.S. Appl. No. 10/674,268, 14 pages.
Advisory Action dated May 22, 2006, U.S. Appl. No. 10/674,268, 4 pages.
Notice of Appeal dated May 31, 2006, U.S. Appl. No. 10/674,268, 2 pages.
Request for Continued Examination and Response to Office Action Made Final and Advisory Action dated Aug. 31, 2006, U.S. Appl. No. 10/674,268, 14 pages.
Final Office Action dated Sep. 15, 2006, U.S. Appl. No. 10/674,268, 8 pages.
Notice of Appeal dated Mar. 15, 2007, U.S. Appl. No. 10/674,268, 2 pages.
Request for Continued Examination and Response to Office Action Made Final dated Jul. 12, 2007, 16 pages.
Final Office Action dated Aug. 2, 2007, U.S. Appl. No. 10/674,268, 9 pages.
Response to Office Action Made Final, dated Oct. 8, 2007, U.S. Appl. No. 10/674,268, 11 pages.
Declaration Under Rule 1.131, dated Oct. 8, 2007, U.S. Appl. No. 10/674,268, 30 pages.
Advisory Action dated Oct. 25, 2007, U.S. Appl. No. 10/674,268, 14 pages.
Request for Continued Examination dated Oct. 30, 2007, U.S. Appl. No. 10/674,268, 2 pages.
Declaration Under Rule 1.131 dated Feb. 12, 2008, U.S. Appl. No. 10/674,268, 2 pages.
Interview Summary dated Mar. 3, 2008, U.S. Appl. No. 10/674,268, 3 pages.
Final Office Action dated Apr. 10, 2008, U.S. Appl. No. 10/674,268 6 pages.
Amendment and Response to Final Office Action dated Sep. 22, 2008, 17 pages.
Advisory Action dated Sep. 30, 2008, U.S. Appl. No. 10/674,268, 7 pages.
Notice of Appeal dated Oct. 10, 2008, U.S. Appl. No. 10/674,268, 2 pages.
Request for Continued Examination and Amendment and Response to Advisory Action of Sep. 30, 2008 and to Office Action of Apr. 10, 2008, dated Apr. 10, 2009, U.S. Appl. No. 10/674,268, 11 pages.
Office Action dated May 19, 2009, U.S. Appl. No. 10/674,268, 11 pages.
Amendment and Response to Office Action dated Oct. 19, 2009, U.S. Appl. No. 10/674,268, 11 pages.
Final Office Action dated Nov. 18, 2009, U.S. Appl. No. 10/674,268, 11 pages.
Examiner's Interview Summary dated Feb. 23, 2010, U.S. Appl. No. 10/674,268, 4 pages.
Notice of Appeal and Interview Summary dated May 18, 2010, U.S. Appl. No. 10/674,268, 2 page.
Examiner's Interview Summary dated May 20, 2010, U.S. Appl. No. 10/674,268, 4 pages.
Request for Continued Examination, Amendment and Response to Final Office Action, U.S. Appl. No. 10/674,268, dated Dec. 17, 2010, 12 pages.
Office Action dated Jan. 12, 2011, U.S. Appl. No. 10/674,268, 14 pages.
Amendment and Response to Office Action dated Jun. 13, 2011, U.S. Appl. No. 10/674,268, 13 pages.
Office Action dated Jul. 6, 2011, U.S. Appl. No. 10/674,268, 12 pages.
Notice of Allowance and Fee(s) Due dated Oct. 19, 2011, U.S. Appl. No. 10/674,268, 7 pages.
Office Action (Restriction Requirement) dated Jun. 17, 2005, U.S. Appl. No. 10/792,648, 10 pages.
Response to Restriction Requirement dated Jun. 29, 2005, U.S. Appl. No. 10/792,648, 8 pages.
Notice of Allowance and Fee(s) Due and Interview Summary dated Jul. 29, 2005, U.S. Appl. No. 10/792,648, 12 pages.
Request for Continued Examination dated Sep. 14, 2005, U.S. Appl. No. 10/792,648, 2 pages.
Notice of Allowance and Fee(s) Due dated Sep. 30, 2005, U.S. Appl. No. 10/792,648, 5 pages.
Request for Continued Examination dated Oct. 14, 2005, U.S. Appl. No. 10/792,648, 2 pages.
Notice of Allowance and Fee(s) Due dated Feb. 15, 2006, U.S. Appl. No. 10/792,648, 5 pages.
Restriction Requirement dated Oct. 31, 2005, U.S. Appl. No. 10/953,328, 5 pages.
Response to Restriction Requirement dated Nov. 29, 2005, U.S. Appl. No. 10/953,328, 8 pages.
Office Action dated Jan. 5, 2006, U.S. Appl. No. 10/953,328, 18 pages.
Amendment and Response dated Apr. 5, 2006, U.S. Appl. No. 10/953,328, 8 pages.
Office Action dated Apr. 26, 2006, U.S. Appl. No. 10/953,328, 9 pages.
Amendment and Response dated Oct. 26, 2006, U.S. Appl. No. 10/953,328, 14 pages.
Office Action (Restriction Requirement) dated Nov. 17, 2006, U.S. Appl. No. 10/953,328, 7 pages.
Response to Restriction Requirement dated Dec. 15, 2006, U.S. Appl. No. 10/953,328, 9 pages.
Final Office Action dated Jan. 18, 2007, U.S. Appl. No. 10/953,328, 13 pages.

(56) References Cited

OTHER PUBLICATIONS

Request for Continued Examination and Amendment and Response to Final Office Action dated Jul. 12, 2007, U.S. Appl. No. 10/953,328, 17 pages.
Final Office Action dated Aug. 7, 2007, U.S. Appl. No. 10/953,328, 11 pages.
Amendment and Response to Final Office Action dated Oct. 5, 2007, U.S. Appl. No. 10/953,328, 8 pages.
Declaration Under Rule 1.131 filed Oct. 5, 2007, U.S. Appl. No. 10/953,328, 38 pages.
Request for Continued Examination dated Oct. 29, 2007, U.S. Appl. No. 10/953,328, 2 pages.
Advisory Action dated Nov. 1, 2007, U.S. Appl. No. 10/953,328, 4 pages.
Office Action dated Dec. 13, 2007, U.S. Appl. No. 10/953,328, 8 pages.
Declaration Under Rule 1.131 dated Feb. 12, 2008, U.S. Appl. No. 10/953,328, 2 pages.
Interview Summary dated Feb. 26, 2008, U.S. Appl. No. 10/953,328, 2 pages.
Amendment and Response to Office Action dated Apr. 14, 2008, U.S. Appl. No. 10/953,328, 28 pages.
Final Office Action dated Jun. 3, 2008, U.S. Appl. No. 10/953,328, 8 pages.
Amendment After Final (Under 37 C.F.R. 1.116) dated Nov. 3, 2008, U.S. Appl. No. 10/953,328, 19 pages.
Request for Continued Examination dated Nov. 25, 2008, U.S. Appl. No. 10/953,328, 2 pages.
Advisory Action dated Dec. 3, 2008, U.S. Appl. No. 10/953,328, 7 pages.
Final Office Action dated Jan. 21, 2009, U.S. Appl. No. 10/953,328, 9 pages.
Request for Continued Examination and Amendment and Response to Final Office Action dated May 21, 2009, U.S. Appl. No. 10/953,328, 22 pages.
Supplementary Declaration Pursuant to 37 C.F.R. 1.131 filed May 27, 2009, U.S. Appl. No. 10/953,328, 27 pages.
Interview Summary dated Jun. 1, 2009, U.S. Appl. No. 10/953,328, 3 pages.
Office Action dated Jun. 22, 2009, U.S. Appl. No. 10/953,328, 9 pages.
Amendment and Response to Office Action dated Sep. 22, 2009, U.S. Appl. No. 10/953,328, 9 pages.
Final Office Action dated Oct. 23, 2009, U.S. Appl. No. 10/953,328, 9 pages.
Notice of Appeal dated Feb. 23, 2010, U.S. Appl. No. 10/953,328, 1 page.
Appeal Brief dated Apr. 23, 2010, U.S. Appl. No. 10/953,328, 49 pages.
Examiner's Answer dated May 24, 2010, U.S. Appl. No. 10/953,328, 8 pages.
Decision on Appeal dated May 11, 2011, U.S. Appl. No. 10/953,328, 9 pages.
Office Action dated May 18, 2011, U.S. Appl. No. 10/953,328, 9 pages.
Amendment and Response to Office Action and Terminal Disclaimer dated Aug. 18, 2011, U.S. Appl. No. 10/953,328, 9 pages.
Terminal Disclaimer dated Sep. 2, 2011, U.S. Appl. No. 10/953,328, 2 pages.
Notice of Allowance and Fee(s) Due dated Sep. 21, 2011, U.S. Appl. No. 10/953,328, 11 pages.
Office Action dated Oct. 23, 2006, U.S. Appl. No. 11/206,718, 12 pages.
Amendment and Response dated Apr. 23, 2007, U.S. Appl. No. 11/206,718, 5 pages.
Terminal Disclaimer dated Apr. 23, 2007, U.S. Appl. No. 11/206,718, 2 pages.
Notice of Allowance and Fee(s) Due dated May 16, 2007, 7 pages.
Office Action (Restriction Requirement) dated Dec. 7, 2005, U.S. Appl. No. 11/223,718, 5 pages.
Amendment and Response dated Jan. 6, 2006, U.S. Appl. No. 11/223,718, 5 pages.
Office Action dated Mar. 15, 2006, U.S. Appl. No. 11/223,718, 7 pages.
Amendment and Response dated Sep. 14, 2006, U.S. Appl. No. 11/223,718, 18 pages.
Final Office Action dated Oct. 2, 2006, U.S. Appl. No. 11/223,718, 8 pages.
Notice of Appeal dated Apr. 2, 2007, U.S. Appl. No. 11/223,718, 2 pages.
Request for Continued Examination and Response to Final Office Action dated Jun. 26, 2007, U.S. Appl. No. 11/223,718, 21 pages.
Final Office Action dated Jul. 20, 2007, U.S. Appl. No. 11/223,718, 10 pages.
Request for Continued Examination and Response to Final Office Action dated Oct. 2, 2007, U.S. Appl. No. 11/223,718, 10 pages.
Declaration Under Rule 1.131 filed Oct. 2, 2007, U.S. Appl. No. 11/223,718, 19 pages.
Office Action dated Oct. 30, 2007, U.S. Appl. No. 11/223,718, 9 pages.
Response to Office Action dated Nov. 30, 2007, U.S. Appl. No. 11/223,718, 19 pages.
Final Office Action dated Jan. 9, 2008, U.S. Appl. No. 11/223,718, 9 pages.
Declaration Under Rule 1.131 dated Feb. 12, 2008, U.S. Appl. No. 11/223,718, 2 pages.
Interview Summary dated Feb. 25, 2008, U.S. Appl. No. 11/223,718, 2 pages.
Amendment After Final Under 37 C.F.R. 1.116 dated Apr. 9, 2008, U.S. Appl. No. 11/223,718, 39 pages.
Advisory Action dated Apr. 23, 2008, U.S. Appl. No. 11/223,718, 5 pages.
Notice of Appeal dated Jun. 9, 2008, U.S. Appl. No. 11/223,718, 2 pages.
Request for Continued Examination and Amendment After Final Under 37 C.F.R. 1.114 dated Oct. 9, 2008, 24 pages.
Final Office Action dated Nov. 17, 2008, U.S. Appl. No. 11/223,718, 11 pages.
Request for Continued Examination and Amendment and Response to Final Office Action dated May 18, 2009, U.S. Appl. No. 11/223,718, 19 pages.
Supplementary Declaration filed May 18, 2009, U.S. Appl. No. 11/223,718, 27 pages.
Notice of Non-Compliant Amendment dated May 21, 2009, U.S. Appl. No. 11/223,718, 2 pages.
Response to Notice of Non-Compliant Amendment dated Jun. 22, 2009, U.S. Appl. No. 11/223,718, 16 pages.
Office Action dated Jul. 24, 2009, U.S. Appl. No. 11/223,718, 12 pages.
Amendment and Response to Office Action dated Oct. 26, 2009, U.S. Appl. 11/223,718, 9 pages.
Final Office Action dated Dec. 2, 2009, U.S. Appl. No. 11/223,718, 10 pages.
Examiner's Interview Summary dated Mar. 23, 2010, U.S. Appl. No. 11/223,718, 4 pages.
Examiner's Interview Summary dated May 20, 2010, U.S. Appl. No. 11/223,718, 4 pages.
Notice of Appeal and Interview Summary dated Jun. 2, 2010, U.S. Appl. No. 11/223,718, 3 pages.
Request for Continued Examination and Amendment and Response to Final Office Action dated Jan. 3, 2011, U.S. Appl. No. 11/223,718, 11 pages.
Office Action dated Jan. 24, 2011, U.S. Appl. No. 11/223,718, 13 pages.
Amendment and Response to Office Action dated Jun. 24, 2011, U.S. Appl. No. 11/223,718, 14 pages.
Final Office Action dated Jul. 14, 2011, U.S. Appl. No. 11/223,718, 5 pages.
Request for Continued Examination and Amendment and Response to Final Office Action dated Sep. 22, 2011, U.S. Appl. No. 11/223,718, 7 pages.
Notice of Allowance and Fee(s) Due dated Nov. 28, 2011, U.S. Appl. No. 11/223,718, 8 pages.

(56) References Cited

OTHER PUBLICATIONS

Office Action (Restriction Requirement) dated Mar. 10, 2009, U.S. Appl. No. 11/860,232, 6 pages.
Amendment and Response to Restriction Requirement dated Apr. 10, 2009, U.S. Appl. No. 11/860,232, 5 pages.
Interview Summary dated Jun. 4, 2009, U.S. Appl. No. 860,232, 3 pages.
Notice of Allowance and Fee(s) Due dated Aug. 7, 2009, U.S. Appl. No. 11/860,232, 17 pages.
Request for Continued Examination dated Nov. 6, 2009, U.S. Appl. No. 11/860,232, 1 page.
Interview Summary dated Nov. 16, 2009, U.S. Appl. No. 11/860,232, 15 pages.
Notice of Allowance and Fee(s) Due dated Dec. 2, 2009, U.S. Appl. No. 11/860,232, 4 pages.
Requestor Comments Responsive to Patent Owner's Petition Under 37 C.F.R. 1.181, U.S. Appl. No. 95/002,396, filed Sep. 5, 2013, 35 pages.
Requestor Comments Responsive to Patent Owner's Petition Under 37 C.F.R. 1.181, U.S. Appl. No. 95/002,405, filed Sep. 4, 2013, 34 pages.
Requestor Comments Responsive to Patent Owner's Petition Under 37 C.F.R. 1.181, U.S. Appl. No. 95/002,411, filed Sep. 4, 2013, 34 pages.
Third Party Requestor's Comments Under 35 U.S.C. 314(b)(2) and 37 C.F.R. 1.951(b) in Inter Partes Reexamination of U.S. Pat. No. 8,124,072, U.S. Appl. No. 95/002,396, filed Sep. 5, 2013, 38 pages.
Third Party Requestor's Comments Under 35 U.S.C. 314(b)(2) and 37 C.F.R. 1.951(b) in Inter Partes Reexamination of U.S. Pat. No. 8,105,583, U.S. Appl. No. 95/002,405, filed Sep. 4, 2013, 36 pages.
Third Party Requestor's Comments Under 35 U.S.C. 314(b)(2) and 37 C.F.R. 1.951(b) in Inter Partes Reexamination of U.S. Pat. No. 8,147,826, U.S. Appl. No. 95/002,411, filed Sep. 4, 2013, 36 pages.
Decision on Petition Under 37 CFR 1.181 in Inter Partes Reexamination of U.S. Pat. No. 8,124,072, U.S. Appl. No. 95/002,396, dated Nov. 6, 2013, 5 pages.
Decision on Petition Under 37 CFR 1.181 in Inter Partes Reexamination of U.S. Pat. No. 8,105,583, U.S. Appl. No. 95/002,405, dated Nov. 6, 2013, 5 pages.
Decision on Petition Under 37 CFR 1.181 in Inter Partes Reexamination of U.S. Pat. No. 8,147,826, U.S. Appl. No. 95/002,411, dated Nov. 6, 2013, 5 pages.
Office Action dated Sep. 27, 2013, U.S. Appl. No. 13/966,063, 10 pages.
Amendment and Response to Office Action dated Oct. 11, 2013, U.S. Appl. No. 13/357,402, 9 pages.
Terminal Disclaimer (U.S. Appl. No. 13/365,244) dated Oct. 11, 2013, U.S. Appl. No. 13/357,402, 2 pages.
Terminal Disclaimer (U.S. Pat. No. 8,124,072) dated Oct. 11, 2013, U.S. Appl. No. 13/357,402, 2 pages.
Terminal Disclaimer (U.S. Pat. No. 8,105,583) dated Oct. 11, 2013, U.S. Appl. No. 13/357,402, 2 pages.
Notice of Allowance and Fee(s) Due dated Oct. 29, 2013, U.S. Appl. No. 13/357,402, 7 pages.
Amendment and Response to Office Action dated Dec. 27, 2013, U.S. Appl. No. 13/966,03, 12 pages.
Office Action dated Apr. 30, 2013, U.S. Appl. No. 13/365,244, 10 pages.
Amendment and Response to Office Action dated Jul. 30, 2013, U.S. Appl. No. 13/365,244, 8 pages.
Terminal Disclaimer (U.S. Pat. No. 8,124,072) dated Jul. 30, 2013, U.S. Appl. No. 13/365,244, 2 pages.
Terminal Disclaimer (U.S. Appl. No. 13/357,402) dated Jul. 30, 2013, U.S. Appl. No. 13/365,244, 2 pages.
Terminal Disclaimer (U.S. Pat. No. 8,105,583) dated Jul. 30, 2013, U.S. Appl. No. 13/365,244, 2 pages.
Notice of Allowance and Fee(s) Due dated Aug. 21, 2013, U.S. Appl. No. 13/365,244, 6 pages.
English translation of JP S57-042616, Furonto Sangyo KK, Absorption improved ubiquinon formulation, 1982.
First Office Action dated Feb. 20, 2014, U.S. Appl. No. 14/141,968, filed Dec. 27, 2013, 31 pages.
First Office Action dated Mar. 18, 2014, U.S. Appl. No. 14/165,319, filed Jan. 27, 2014, 29 pages.
U.S. Appl. No. 14/560,136, filed Dec. 4, 2014, now abandoned.
U.S. Appl. No. 14/165,319, filed Jan. 27, 2014, now issued as U.S. Pat. No. 8,932,585.
U.S. Appl. No. 13/357,402, filed Jan. 24, 2012, now issued as U.S. Pat. No. 8,658,161.
U.S. Appl. No. 10/953,328, filed Sep. 29, 2004, now issued as U.S. Pat. No. 8,105,583.
U.S. Appl. No. 10/674,268, filed Sep. 29, 2003, now issued as U.S. Pat. No. 8,124,072.

\* cited by examiner

SOLUBILIZED COQ-10

CROSS-REFERENCE TO RELATED APPLICATION

This application is a continuation of U.S. application Ser. No. 14/560,136, filed Dec. 4, 2014, which is a continuation of U.S. application Ser. No. 14/165,319, filed Jan. 27, 2014, issued as U.S. Pat. No. 8,932,585, which is a continuation of U.S. application Ser. No. 13/357,402, filed Jan. 24, 2012, issued as U.S. Pat. No. 8,658,161, which is a continuation of U.S. application Ser. No. 10/953,328, filed Sep. 29, 2004, issued as U.S. Pat. No. 8,105,583, which is a Continuation-in-Part of U.S. application Ser. No. 10/674,268, filed Sep. 29, 2003, issued as U.S. Pat. No. 8,124,072, the contents of which are hereby incorporated herein in their entirety for all purposes.

FIELD OF THE INVENTION

The present invention relates to the solubilization of coenzyme Q-10 and analogs thereof in monoterpenes, thereby providing increased bioavailability in delivery.

BACKGROUND OF THE INVENTION

CoQ-10 (coenzyme Q10) is a fat-soluble quinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 can be synthesized in the body or it can be derived from dietary sources. Situations may arise, however, when the need for CoQ-10 surpasses the body's ability to synthesize it. CoQ-10 can be absorbed by oral supplementation as evidenced by significant increases in serum CoQ-10 levels after supplementation.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa Several clinical trials have shown CoQ-10 to be effective in supporting blood pressure and cholesterol levels. Furthermore, CoQ-10 has also been shown to improve cardiovascular health. CoQ-10 has been implicated as being an essential component in thwarting various diseases such as certain types of cancers. These facts lead many to believe that CoQ-10 supplementation is vital to an individual's well being.

CoQ-10 is sparingly soluble in most hydrophilic solvents such as water. Therefore, CoQ-10 is often administered in a powdered form, as in a tablet or as a suspension. However, delivery of CoQ-10 by these methods limits the bioavailability of the material to the individual.

There is a need in the art for an improved methodology to deliver increased amount of bioavailable CoQ-10 to an individual in need thereof.

BRIEF SUMMARY OF THE INVENTION

The present invention pertains to the surprising discovery that ubiquinone (CoQ-10) and related analogs thereof can be readily dissolved in varying concentrations in monoterpenes. Generally, until the present discovery, most CoQ-10 liquid delivery methods could solubilize only up to about 5% by weight of the CoQ-10 in the "solvent". Typical solvents included various oils or the CoQ-10 was held in suspension. The present invention provides the ability to solubilize CoQ-10 in monoterpenes in concentrations of up to about 60% (weight to weight) without the need to aggressively heat the solution or with gentle warming. In particular, the solubilization of the CoQ-10 with monoterpenes can be accomplished at ambient temperatures.

In one aspect, the present invention pertains to compositions that include coenzyme Q-10 or an analog thereof with a sufficient quantity of a monoterpene that is suitable to solubilize said coenzyme Q-10 and a pharmaceutically acceptable carrier. Generally, about 30 to about 45% of the CoQ-10 (by weight) is solubilized in the monoterpene. In particular, the monoterpene is limonene. The compositions of the invention are useful as dietary supplements or as nutriceuticals.

In particular, the compositions of the invention are included in a soft gelatin (soft gel) capsule. Typically, the soft gelatin capsule includes at least 5% by weight of coenzyme Q-10 or an analog thereof solubilized in a monoterpene. Typical monoterpenes include, for example, perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

In another embodiment, the present invention pertains to methods for delivery of an effective amount of bioavailable CoQ-10 to an individual. The method includes providing CoQ-10 solubilized in a monoterpene, such that an effective amount of CoQ-10 is provided to the individual.

In still another embodiment, the present invention also includes packaged formulations of the invention that include a monoterpene as a solvent for the CoQ-10 and instructions for use of the tablet, capsule, elixir, etc.

In one aspect, the present invention provides solubilized coenzyme Q-10 compositions that include coenzyme Q-10 or an analog thereof, a sufficient quantity of a monoterpene suitable to solubilize said coenzyme Q-10 or analog thereof, and an acceptable carrier. The compositions provide a percentage of coenzyme Q-10 dosage that is absorbed by an individual of between about 5 percent and about 12 percent of said coenzyme Q-10 or analog thereof that is administered. The ranges of absorbed coenzyme Q-10 are from about 5 percent to about 12 percent, from about 6 percent to about 10 percent, and from about 6.5 percent to about 9.5 percent, based on the dosage of coenzyme Q-10 or analog thereof taken.

In another aspect, the present invention provides solubilized coenzyme Q-10 compositions that include coenzyme Q-10 or an analog thereof, a sufficient quantity of a monoterpene suitable to solubilize said coenzyme Q-10 or analog thereof, and an acceptable carrier. The compositions provide a bioavailable steady state plasma level of coenzyme Q-10 or an analog thereof of between about 2.5 µg/ml to about 3.5 µg/ml. Suitable ranges of steady state plasma levels of coenzyme Q-10 or analog thereof are from about 2.5 µg/ml to about 3.5 µg/ml, from about 2.75 µg/ml to about 3.25 µg/ml and from about 2.75 µg/ml to about 3.0 µg/ml, based on the dosage of coenzyme Q-10 or analog thereof taken.

In still yet another aspect, the present invention provides compositions that include solubilized coenzyme Q-10 or an analog thereof, a sufficient quantity of a monoterpene suitable to solubilize said coenzyme Q-10 or analog thereof, and an acceptable carrier. The compositions provide a peak plasma level of coenzyme Q-10 or analog thereof of between about 2.1 µg/ml to about 3.0 µg/ml. Suitable ranges of peak plasma levels of coenzyme Q-10 or analog thereof are from about 2.1 µg/ml to about 3.0 µg/ml, from about 2.2 µg/ml to about 2.8 µg/ml and from about 2.2 µg/ml to about 2.5 µg/ml.

In another aspect, the present invention pertains to methods for delivery of an effective amount of bioavailable CoQ-10 to an individual. The methods include providing CoQ-10 solubilized in a monoterpene, such that an effective amount of CoQ-10 is provided to the individual so that the dosage absorbed, the steady state plasma levels of coenzyme Q-10, or the peak plasma levels of coenzyme Q-10 are sustained.

In still another embodiment, the present invention also includes packaged formulations of the invention that include a monoterpene as a solvent for the CoQ-10 and instructions for use of the tablet, capsule, elixir, etc. so that the dosage absorbed, the steady state plasma levels of coenzyme Q-10, or the peak plasma levels of coenzyme Q-10 are sustained.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
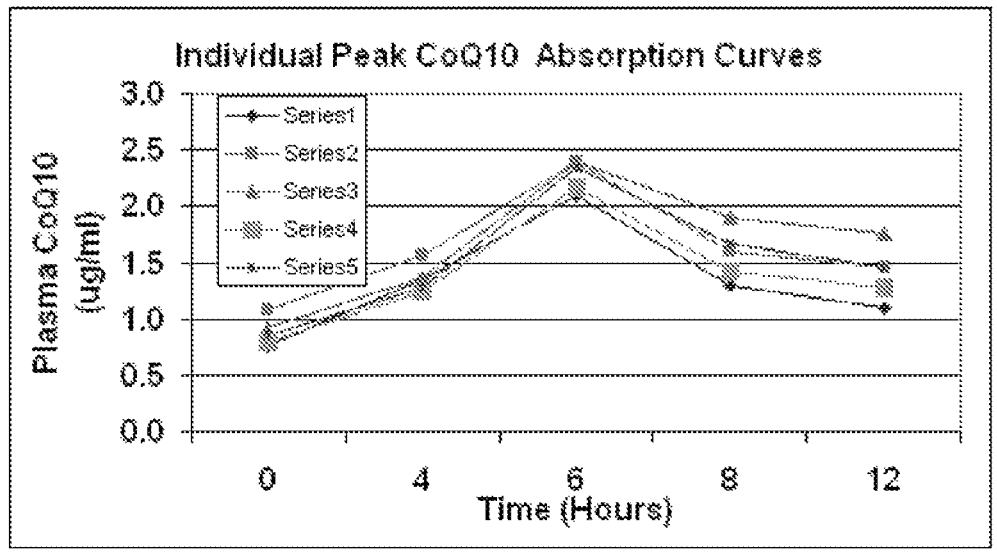
FIG. 1 depicts individual single dose (60 mg) peak absorption curves for solubilized coenzyme Q-10.

The present invention pertains to the surprising discovery that ubiquinone (CoQ-10) can be readily dissolved in varying concentrations in monoterpenes. CoQ-10 is found in most living organisms, and is essential for the production of cellular energy. Ubiquinone is a naturally occurring hydrogen carrier in the respiratory chain (coenzyme Q) and structurally, it is a 2,3-dimethoxy-5-methyl-1,4-benzoquinone with a multiprenyl side chain, the number of isoprene units varying depending upon the organism from which it is derived. CoQ-10 analogs include reduced and semi-reduced CoQ-10 and ubiquinone derivatives described, for example, in WO 8803015, the teachings of which are incorporated herein by reference.

Generally, until the present discovery, most CoQ-10 liquid delivery methods could solubilize only up at most about 10% by weight of the CoQ-10 in the solvent. Typical solvents included oils or the CoQ-10 was held in an aqueous suspension. Alternatively, the CoQ-10 was provided as a solid in a tablet or powder.

The present invention provides the ability to solubilize CoQ-10 and analogs thereof in monoterpenes, as defined herein, in concentrations of up to about 60% (weight to weight) without the need to heat the solution. In one aspect, the monoterpene solubilizes CoQ-10 from about 0.1 percent by weight to about 45 percent by weight.

In particular, the solubilization of the CoQ-10 and analogs thereof with monoterpenes can be accomplished at ambient temperatures. In one aspect, from about 5 to about 50 percent (weight CoQ-10/weight solvent) CoQ-10 can be solubilized in a monoterpene. In another aspect, from about 15 to about 40 percent w/w can be solubilized and in still another aspect, from about 20 to about 35 percent w/w CoQ-10 can be solubilized in a monoterpene.

The phrase "sufficient quantity of a monoterpene suitable to solubilize coenzyme Q-10" is therefore intended to mean that that amount of a monoterpene that will dissolve CoQ-10 under a given set of conditions, generally, those at ambient temperature. This determination should be understood by one skilled in the art and can be determined by methods known in the art, such as by solubility studies.

One of the particular advantages of utilizing monoterpenes in combination with CoQ-10 and analogs thereof is that the enzyme is dissolved by the monoterpene. That is, many formulations currently in the marketplace have CoQ-10 present as a suspension; a situation where not all the CoQ-10 is dissolved. This reduces efficacy and the bioavailability of the CoQ-10. The present invention eliminates this disadvantage by solubilizing the CoQ-10 in the monoterpene.

A particular advantage in using monoterpenes is that the CoQ-10 or analog thereof does not have to be heated to dissolve into solution. This is important so that the CoQ-10 or analog thereof does not degrade upon dissolution.

The term "monoterpene" as used herein, refers to a compound having a 10-carbon skeleton with non-linear branches. A monoterpene refers to a compound with two isoprene units connected in a head-to-end manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein. Suitable examples of monoterpenes include, but are not limited to, limonene, pinene, cintronellol, terpinene, nerol, menthane, carveol, S-linalool, safrol, cinnamic acid, apiol, geraniol, thymol, citral, carvone, camphor, etc. and derivatives thereof. For information about the structure and synthesis of terpenes, including terpenes of the invention, see Kirk-Othmer Encyclopedia of Chemical Technology, Mark, et al., eds., 22:709-762 3d Ed (1983), the teachings of which are incorporated herein in their entirety.

In particular, suitable limonene derivatives include perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

Formulation of the CoQ-10 and analogs thereof can be accomplished by many methods known in the art. For example, the solubilized CoQ-10 or analog thereof can be formulated in a suspension, an emulsion, an elixir, a solution, a caplet that harbors the liquid, or in a soft gelatin capsule. Often the formulation will include an acceptable carrier, such as an oil, or other suspending agent.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are considered dietary supplements useful to the increase the amounts of CoQ-10 and analogs thereof in the individuals in need thereof.

Alternatively, the formulations of the invention are also considered to be nutraceuticals. The term "nutraceutical" is recognized in the art and is intended to describe specific chemical compounds found in foods that may prevent disease. CoQ-10 or an analog thereof are such compounds.

The formulations of the invention can further include various ingredients to help stabilize, or help promote the bioavailability of the CoQ-10 and analogs thereof, or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

L-carnitine is recognized in the art and facilitates transport of materials through the mitochondrial membrane. L-carnitine is an essential fatty acid metabolism cofactor that helps to move fatty acids to the mitochondria from the cytoplasm. This is an important factor as this is where CoQ-10 uptake occurs.

In one aspect of the present invention, L-carnitine is included in soft gel formulations in combination with CoQ-10 or an analog thereof. Suitable ratios of L-carnitine and CoQ-10 are known in the art and include those described in U.S. Pat. No. 4,599,232, issued to Sigma Tau Industrie Faramaceutiche Riunite S.p.A. on Jul. 8, 1986, the teachings of which are incorporated herein in their entirety. In particular, combinations of limonene, CoQ-10 and L-carnitine in soft gel formulations are of importance. The present invention provides the advantage of solvating large amounts (relative to that of current state of the art) of CoQ-10 in limonene in a soft gel capsule along with an additive, such as L-carnitine.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, carnosic acid and rosmanol found in rosemary and hawthorn extract, proanthocyanidins such as those found in grapeseed or pine bark extract, and green tea extract.

The term "flavonoid" as used herein is recognized in the art and is intended to include those plant pigments found in many foods that are thought to help protect the body from cancer. These include, for example, epi-gallo catechin gallate (EGCG), epi-gallo catechin (EGC) and epi-catechin (EC).

The phrase "solubilized CoQ-10 and analogs thereof" is intended to mean that the coenzyme Q-10 is solvated by the lipophilic materials incorporated into the soft gel capsule. Typical capsules that contain CoQ-10 or an analog thereof include the coenzyme or analog as a dry powder or as a suspension of crystals. It is believed that the powder or crystallinity of the coenzyme does not facilitate absorption by the cells. The present invention overcomes this disadvantage by providing formulations wherein the coenzyme is not in a powdered or crystalline form. Microscopic evaluations of the lipophilic formulations do not show crystals of the coenzyme. Consequently, it is believed that the solvated coenzyme can more easily pass into cells. This is highly advantageous in delivering increased amounts of the coenzyme into an individual's physiological make up.

Any dosage form, and combinations thereof, are contemplated by the present invention. Examples of such dosage forms include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

For example, health bars can be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules can be prepared, for example, without limitation, by dispersing the formulation in an appropriate vehicle (e.g. rice bran oil, monoterpene and/or beeswax) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally limonene, in combination with rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams.

For example, a soft gel capsule can be prepared by mixing a 35% solution of CoQ-10 and limonene (w/w) (e.g., 104 milligrams of CoQ-10 in 193.14 milligrams of limonene) with between about 0.01 grams and about 0.4 grams (e.g., 0.1 grams) tocopherol, between about 200 grams and about 250 grams (e.g., 225 grams) rice bran oil and between about 0.01 grams and about 0.5 grams betacarotene (e.g. about 0.02 grams). The mixture is then combined with encapsulated within a gelatin capsule as described above.

The present invention also provides packaged formulations of a monoterpene with CoQ-10 and instructions for use of the tablet, capsule, elixir, etc. Typically, the packaged formulation, in whatever form, is administered to an individual in need thereof that requires and increase in the amount of CoQ-10 in the individual's diet. Typically, the dosage requirements is between about 1 to about 4 dosages a day.

CoQ-10 has been implicated in various biochemical pathways and is suitable for the treatment of cardiovascular conditions, such as those associated with, for example, statin drugs that effect the body's ability to produce CoQ-10 naturally. CoQ-10 has also been implicated in various periodontal diseases. Furthermore, CoQ-10 has been implicated in mitochondrial related diseases and disorders, such as the inability to product acetyl coenzyme A, neurological disorders, for example, such as Parkinson's disease and, Prater-Willey syndrome.

The following examples are intended to be illustrative only and should not be considered limiting.

EXAMPLES

Formulations of CoQ-10 can be prepared in the following ratios by mixing the components together and then placing into a soft gel capsule.

| Component | Example 1 | Example 2 |
|---|---|---|
| CoQ-10 | 104.09 mg | 104.09 mg |
| Mixed Tocopherols (372 IU/g) | 269.03 mg | 269.03 mg |
| Rice Bran Oil | 176.02 mg | — |
| Natural Beta Carotene (20% by weight) | 10.05 mg | 10.05 mg |
| Yellow Beeswax | 20.0 mg | — |
| D-limonene | — | 196.02 mg |
| Total weight | 580 mg | 580 mg |

Example 2 demonstrates that the use of limonene solubilizes CoQ-10 without the requirement of beeswax and/or rice bran oil being present. Examples 1 and 2 can be incorporated into soft gel capsules by standard methods known in the art.

| Component | Example 3 | Example 4 |
|---|---|---|
| CoQ-10 | 17.95 g | 17.95 g |
| EPAX 2050TG | 48.77 g | 45.49 g |
| D-Limonene | 35.70 g | 35.70 g |
| 5-67 Tocopherol (1000 IU/g) | — | 0.86 g |

Examples 3 and 4 demonstrate that CoQ-10 can be solubilized in scalable quantities. Additives, such as EPAX 2050 TG (an ω-3 oil; 20% EPA/50% DHA as triglycerides, remainder fatty acid/triglycerides; Pronova Biocare) and tocopherols (5-67 Tocopherol; BD Industries) can easily be incorporated into such limonene containing formulations. The resultant mixtures contained approximately 100 mg of CoQ-10 per soft gel capsule. Preparation of the soft gel capsules was accomplished by methods well known in the art.

| Component | Example 5 | Example 6 |
|---|---|---|
| CoQ-10 (98%) | 62.45 mg | 62.45 mg |
| Vitamin E mixed tocopherols (700 mg/g) | 69.19 mg | 161.3. mg |
| D-Limonene | 118.1 mg | none |
| Soybean oil | 30.26 mg | none |
| 5-67 Tocopherol (1000 IU/g) | 60.0 mg | none |
| yellow beeswax | none | 15.0 mg |
| Rice bran oil | none | 188.71 mg |
| Natural beta Carotene | none | 7.54 mg |
| | mg/capsule | mg/capsule |

Examples 5 and 6 provide a comparison between soft gel capsules prepared with D-limonene and without D-limonene and enzyme CoQ-10. Examples 5 and 6 will be referred to throughout the following paragraphs to show efficacy in delivery with the use of the monoterpene, D-limonene.

The single 60 mg dose peak absorption characteristics and the 28-day 60 mg daily dose steady state bioavailability of the solubilized $CoQ_{10}$ formulation was determined in five (5) normal male (N=3) and female (N=2) volunteers. The peak absorption study was done over 12 hours. For the control sample, the volunteers were in a rested and fasted condition-minimum eight (8) hours. Serial blood samples were taken at 0, 4, 6, 8, and 12 hours after ingesting 60 mg of a softgel product (either solubilized $CoQ_{10}$ (Example 5) or Example 6, a non-solubilized $CoQ_{10}$ formulation. In the steady state bioavailability study, daily doses of 60 mg of the solubilized $CoQ_{10}$ formulation were taken with breakfast. $CoQ_{10}$ in plasma was measured using the hexane extraction and HPLC detection method described in "A New Method to Determine the Level of Coenzyme Q10 in One Drop of Human Blood for Biomedical Research", Manabu Morita and Karl Folkers, Biochem. Biophys. Res. Commun. 191(3), 950-954, 1993, the contents of which are incorporated herein in their entirety. The solubilized $CoQ_{10}$ formulation was a soft gel capsule that contained 60 mg $CoQ_{10}$, 118.1 mg limonene, 30.26 mg soybean oil and vitamin E as described in Example 5. The non-solubilized formulation was a soft gel capsule that contained 60 mg $CoQ_{10}$, 188.71 mg rice bran oil, 161.3 mg vitamin E (and additional additives) as described in Example 6.

Group mean control plasma $CoQ_{10}$ level (0.88±0.13 μg/ml) was in the normal range. Tmax after ingestion of a single 60 mg capsule was in six (6) hours and the mean peak plasma level (Cmax) was 2.28±0.14 μg/ml. The amount of solubilized $CoQ_{10}$ absorbed at Cmax was 4,765.51±825.39 μg or 7.96±1.38% of the ingested dose. With daily dosing the plasma solubilized $CoQ_{10}$ level increased to a mean plateau level of 2.68±0.15 μg/ml in 14 days and remained fairly constant thereafter. The 28-day plasma level was 2.75±0.22 μg/ml. The solubilized $CoQ_{10}$ bioavailability in plasma was 6,498.90±1,634.76 μg, and the area under the plasma time base curve was 42.27±2.29 μg/ml·day. These data demonstrate that the solubilized $CoQ_{10}$ formulation was absorbed significantly ($p<0.001$). The peak absorption of 7.96% of the ingested dose and the steady state bioavailability after 28 days was significantly ($p<0.01$) greater than that found in Example 6.

The solubilized $CoQ_{10}$ formulation (Example 5) absorption is greater than that of most softgel $CoQ_{10}$ products in which $CoQ_{10}$ crystals are suspended in a lipid base and those products that provide only a dried powder composition.

Peak Absorption Characteristics and Steady State Bioavailability of Solubilized $CoQ_{10}$ formulation The use of Coenzyme $Q_{10}$ ($CoQ_{10}$) around the world has surpassed the production capabilities of the Japanese producers. $CoQ_{10}$ is also rapidly entering the clinical consumer market with the positive study reports on heart failure, Parkinson's disease, muscular ataxias, low energy genetic syndromes, statin drug inhibition of $CoQ_{10}$ synthesis and recent publications that show that $CoQ_{10}$ and its precursors in the body inhibit farensyl-transferase and thus turn off the growth and rapid division of cancer cells. With these advances in $CoQ_{10}$ research and the conclusions that plasma $CoQ_{10}$ levels for clinical efficacy should be raised to about 3.2 μg/ml, more companies have been seeking to develop $CoQ_{10}$ products with improved absorption and steady state bioavailability. The absorption of $CoQ_{10}$ is not the same for all $CoQ_{10}$ products found in the market place. In general dry powder delivery systems have 0.5 to 2% peak absorption. Dry powder $CoQ_{10}$ in a lipid base that is incorporated into soft gelatin capsules has better peak absorption (2.0-3.0%). This appears to be dependant on the number and size of the $CoQ_{10}$ crystals in the product.

The following data relate to peak absorption characteristics of a single 60 mg dose and the steady state bioavailability of a daily 60 mg dose for the solubilized $CoQ_{10}$ softgel formulation. Both studies were conducted on the same five (5) normal volunteer subjects. Peak absorption and steady state bioavailability characteristics were compared to that of Example 6 which was collected using a similar study design but different volunteers.

Methods

Five normal volunteers (3 males/2 females) were randomly selected from a screened group of 15 individuals (Table I). The exclusion criteria were: 1) smoker, 2) individual taking a $CoQ_{10}$ product, 3) individual with high plasma cholesterol, 4) individual taking drugs known to interfere with endogenous synthesis or $CoQ_{10}$ absorption, 5) individual on vegetarian diet, and 6) athlete.

TABLE I

Physical Characteristics of Study Volunteers

| VOLUNTEER | AGE YEARS | SEX | HEIGHT INCHES | WEIGHT POUNDS | PLASMA VOLUME MILLILITERS |
|---|---|---|---|---|---|
| PDOB 01 | 43 | F | 63.50 | 147.00 | 3139.00 |
| RFRE 02 | 42 | M | 66.25 | 170.75 | 3720.00 |
| AJOH 03 | 43 | M | 69.50 | 205.00 | 3928.00 |
| SHAL 04 | 26 | M | 70.50 | 192.50 | 3870.00 |
| NJOH 05 | 39 | F | 63.75 | 126.00 | 2520.00 |

After being fully familiarized with the experimental design and their responsibilities, the volunteers had their questions answered by the principle investigator, and read and signed a volunteer consent form. On day 0 of the study, volunteers reported to the testing facility at 0600 in a rested and fasted state-minimum eight (8) hours. Vital signs were taken, an intercath was placed in a forearm vein, and a control blood sample was collected for determining the control $CoQ_{10}$ plasma level. The volunteers were then given a single 60 mg dose of the solubilized $CoQ_{10}$ formulation. This was followed by a breakfast consisting of orange juice or milk (2%) with a bagel or cereal. Blood samples were drawn again at hours 4, 6, 8 and 12; vital signs and safety data were collected simultaneously. Starting with day 1 of the study, the volunteers took 60 mg of solubilized $CoQ_{10}$ formulation daily for the next 28 days. During this time, volunteers followed their regular diet and activity schedules and returned to the testing facility on days 7, 14, 21, and 28 at 0600 in a rested and fasted condition—minimum eight (8) hours—for the purpose of collecting vital signs and safety data, and to have a venous blood sample collected from which plasma $CoQ_{10}$ levels were determined.

All $CoQ_{10}$ samples were collected in vaccutainers containing EDTA to prevent clotting. The samples were cooled in ice water and then centrifuged to separate the plasma from the formed elements. The plasma was pipetted into a sealable transfer container, labeled according to volunteer identification and hour of collection and frozen at $-20°$ centigrade. All plasma samples were shipped overnight in dry ice to an independent laboratory for $CoQ_{10}$ analysis. The method used was that as described in Morita & Folkers (supra) hexane extraction and HPLC detection.

Individual volunteer data points were entered into a Microsoft Excel spreadsheet. Descriptive statistics were used to calculate group means SD and SE. Statistical differences between group control and each group sample for the peak absorption and the steady state weekly levels were determined using a standard t-test for differences between group means. A probability of $p \leq 0.05$ was accepted as significant.

Results

I: Peak Absorption Study

Individual and group means±SE & SD descriptive statistics data for the 60 mg single dose peak absorption study are presented in Table II and the individual data plotted on a 12 hour time base are shown in FIG. 1. Control plasma $CoQ_{10}$ was variable between volunteers (range=0.77-1.09 µg/ml). The group means±SD was 0.88±0.13 µg/ml. This is considered to be in the normal range. Within four hours after ingesting the solubilized $CoQ_{10}$ the plasma levels for the group increased significantly ($p \leq 0.01$) to 1.36±0.12 µg/ml. Peak plasma levels occurred at six (6) hours (Tmax) and the maximum plasma concentration (Cmax) was 2.28±0.14 µg/ml. Thereafter plasma $CoQ_{10}$ rapidly decreased over the next two hours to a mean level of 1.58±0.23 µg/ml during the rapid tissue uptake period of $CoQ_{10}$. The peak absorption kinetics calculated from the peak absorption data are presented in Table IV.

TABLE II

Individual and Group Solubilized $CoQ_{10}$ formulation:
Single Dose (60 mg) Peak Absorption Study

| | Sample Time (Hours) | | | | |
|---|---|---|---|---|---|
| | 0 | 4 | 6 | 8 | 12 |
| Volunteer | | | | | |
| 1 | 0.77 | 1.35 | 2.09 | 1.30 | 1.10 |
| 2 | 1.09 | 1.56 | 2.40 | 1.60 | 1.46 |
| 3 | 0.92 | 1.36 | 2.39 | 1.90 | 1.76 |
| 4 | 0.79 | 1.24 | 2.16 | 1.42 | 1.27 |
| 5 | 0.85 | 1.28 | 2.34 | 1.67 | 1.45 |
| Mean | 0.88 | 1.36 | 2.28 | 1.58 | 1.41 |
| Standard Error | 0.06 | 0.06 | 0.06 | 0.10 | 0.11 |
| Standard Deviation | 0.13 | 0.12 | 0.14 | 0.23 | 0.25 |
| P-value | | 3.24E-05 | 1.57E-06 | 0.000766 | 0.002338 |

The amount of $CoQ_{10}$ absorbed at Cmax was 4,769.51±825.39 µg. When compared to the ingested dose (60,000 µg), the percent of the dose absorbed at Cmax was 7.95±1.38%. In the first two hours after Cmax an average of 2196.14±523.83 µg was distributed out of the blood and into the body cells. The amount was 46.46±9.85% of that absorbed at Cmax.

II: Steady State Plasma $CoQ_{10}$ Bioavailability

Figure 2:
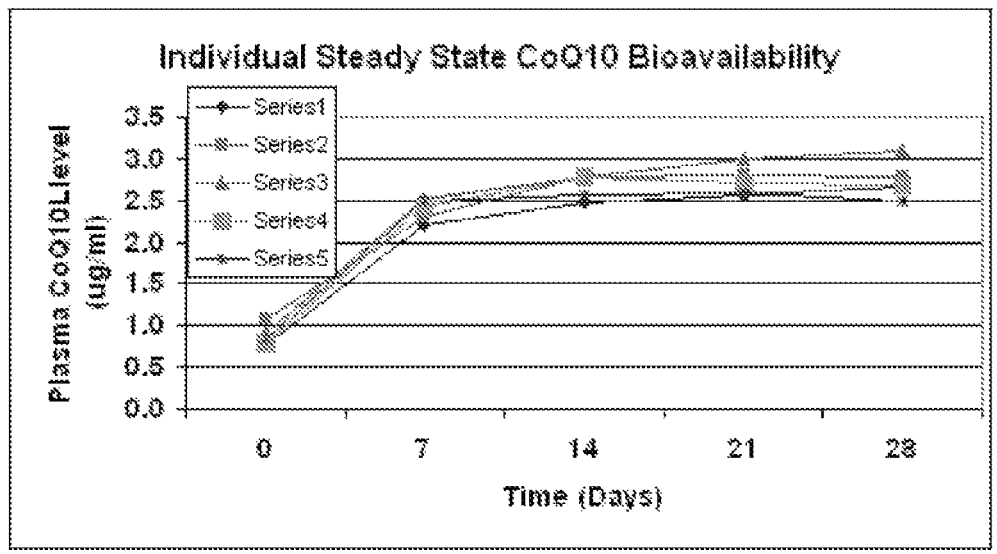
FIG. 2 shows individual daily dose (60 mg/day) steady state plasma coenzyme Q-10 bioavailability curves for the solubilized coenzyme Q-10.
Figure 4:
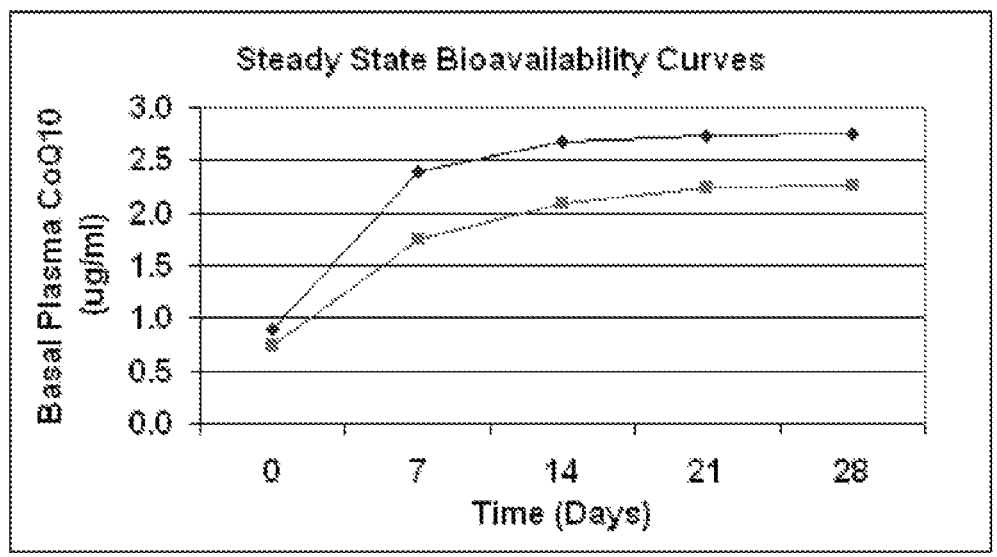
FIG. 4 is a graphical representation of the steady state bioavailability curves for the solubilized coenzyme Q-10 (upper line, ♦)(Example 5) and Example 6 (lower line, ■) at a daily dose of 60 mg/day. Plasma levels at 7, 14, 21 and 28 days were significant ($P<0.01$) for the solubilized coenzyme Q-10 formulation.

Individual and group means±SD descriptive statistics data for the 28-day 60 mg/day steady state plasma $CoQ_{10}$ bioavailability for the solubilized $CoQ_{10}$ formulation are presented in Table III and graphically in FIGS. 2 and 4. Again there was a variation between volunteers. In seven (7) days the basal plasma $CoQ_{10}$ level increased significantly ($p \leq 0.01$) to 2.39±0.13 µg/ml. Plasma levels plateaued for each volunteer between the 7th and 14th day and remained fairly constant thereafter (FIG. 2). At the 28th day the group means plasma $CoQ_{10}$ level was 2.75±0.22 µg/ml ($p \leq 0.001$). The calculated steady state increase in plasma $CoQ_{10}$ was 6,458.90±1,634.76 µg at a constant daily dose of 60 mg/day (Table V). In a steady state condition the group mean relative increase in plasma $CoQ_{10}$ was 314.42±39.07%. The area under the plasma $CoQ_{10}$ and time base curve between days 0 and 28 days ($AUC_{0-28day}$)(AUC denotes area under the curve) is used to equate the $CoQ_{10}$ bioavailability. The AUC for this product was 42.27±2.29 µg/ml·day.

TABLE III

Individual and Group Solubilized CoQ$_{10}$: Steady State (60 mg/day) Plasma CoQ10 Bioavailability Study

|  | Time (Days) | | | | | | AUC (0-28 |
| --- | --- | --- | --- | --- | --- | --- | --- |
|  | 0 | 7 | 14 | 21 | 28 | % Change | day) ug/ml · day |
| Volunteer | | | | | | | |
| 1 | 0.77 | 2.20 | 2.48 | 2.56 | 2.67 | 285.71 | 42.77 |
| 2 | 1.09 | 2.30 | 2.79 | 2.80 | 2.78 | 211.01 | 38.68 |
| 3 | 0.92 | 2.52 | 2.78 | 3.00 | 3.10 | 273.91 | 42.22 |
| 4 | 0.79 | 2.42 | 2.78 | 2.70 | 2.68 | 306.33 | 42.61 |
| 5 | 0.85 | 2.49 | 2.56 | 2.60 | 2.50 | 292.94 | 45.05 |
| Mean | 0.88 | 2.39 | 2.68 | 2.73 | 2.75 | 314.42 | 42.27 |
| Standard Error | 0.06 | 0.06 | 0.07 | 0.08 | 0.10 | 17.47 | 1.02 |
| Standard Deviation | 0.13 | 0.13 | 0.15 | 0.18 | 0.22 | 39.07 | 2.29 |
| p-value |  | 2.65E−05 | 3.11E−06 | 5.13E−06 | 5.13E−06 | | |

TABLE IV

Individual and Group Single Dose Peak Absorption Characteristics for Solubilized CoQ$_{10}$ formulation

|  | Control Plasma Q10 ug/ml | Plasma Cmax ug/ml | Change Plasma Q10 ug/ml | Plasma Vol ml | Change in Plasma Q10 ug | % of Dose Absorbed | Rapid Q10 Distribution ug/ml | Amt. Q10 Distributed ug | % Distributed of Amt. Absorbed |
| --- | --- | --- | --- | --- | --- | --- | --- | --- | --- |
| Volunteer | | | | | | | | | |
| 1 | 0.77 | 2.09 | 1.32 | 3139.00 | 4143.48 | 6.91 | 0.61 | 1914.79 | 46.21 |
| 2 | 1.09 | 2.40 | 1.31 | 3720.00 | 4873.20 | 8.12 | 0.80 | 2976.00 | 61.07 |
| 3 | 0.92 | 2.39 | 1.47 | 3928.00 | 5774.16 | 9.62 | 0.49 | 1924.72 | 33.33 |
| 4 | 0.79 | 2.16 | 1.37 | 3870.00 | 5301.90 | 8.84 | 0.64 | 2476.80 | 46.72 |
| 5 | 0.85 | 2.34 | 1.49 | 2520.00 | 3754.80 | 6.26 | 0.67 | 1688.40 | 44.97 |
| Mean | 0.88 | 2.28 | 1.48 | 3435.40 | 4769.51 | 7.95 | 0.64 | 2196.14 | 46.46 |
| SD | 0.06 | 0.06 | 0.08 | 268.17 | 369.12 | 0.62 | 0.05 | 234.26 | 4.41 |
| SE | 0.13 | 0.14 | 1.39 | 599.65 | 825.39 | 1.38 | 0.11 | 523.83 | 9.85 |

III: Particle and Crystalline Characteristics of Solubilized CoQ$_{10}$

Photomicrographs of solubilized CoQ$_{10}$ (Example 5) and Example 6 showed that Example 6 had many small crystals of CoQ$_{10}$, whereas the solubilized CoQ$_{10}$ (Example 5) showed no crystals, and appeared to be a homogenous distribution of CoQ$_{10}$ molecules in solution.

DISCUSSION

The study determined the peak single dose (60 mg) absorption characteristics and the steady state plasma CoQ$_{10}$ bioavailability in response to a constant daily dose of 60 mg/day for 28 days of solubilized CoQ$_{10}$. The control plasma CoQ$_{10}$ data for the small group (N=5) was in the normal range (Tables 1 &2). The plasma CoQ$_{10}$ increase at Cmax (2.28±0.14 µg/ml) was significantly (p<0.001) above the control level as was the amount of CoQ$_{10}$ added to the plasma at Cmax (Table IV and V).

TABLE V

Individual and Group Solubilized CoQ$_{10}$ (Example 5): Steady State (60 mg/day) CoQ$_{10}$ Bioavailability Study

|  | C-CoQ10 ug/ml | 28 Day ug/ml | Change ug/ml | Plasma Vol ml | Plasma Q Change ug/ml | % Change | AUC (0-28 day) ug/ml · day |
| --- | --- | --- | --- | --- | --- | --- | --- |
| Volunteer | | | | | | | |
| 1 | 0.77 | 2.67 | 1.90 | 3,139.00 | 5,964.10 | 346.75 | 42.77 |
| 2 | 1.09 | 2.78 | 1.69 | 3,720.00 | 6,286.80 | 255.05 | 38.68 |
| 3 | 0.92 | 3.10 | 2.18 | 3,928.00 | 8,563.04 | 336.96 | 42.22 |
| 4 | 0.79 | 2.68 | 1.89 | 3,870.00 | 7,314.30 | 339.24 | 42.61 |
| 5 | 0.85 | 2.50 | 1.65 | 2,525.00 | 4,166.25 | 294.12 | 45.05 |
| Mean | 0.88 | 2.75 | 1.86 | 3,436.40 | 6,458.90 | 314.42 | 42.27 |
| Standard Error | 0.06 | 0.10 | 0.09 | 267.32 | 731.09 | 17.47 | 1.02 |
| Standard Deviation | 0.13 | 0.22 | 0.21 | 597.75 | 1,634.76 | 39.07 | 2.29 |

Figure 3:
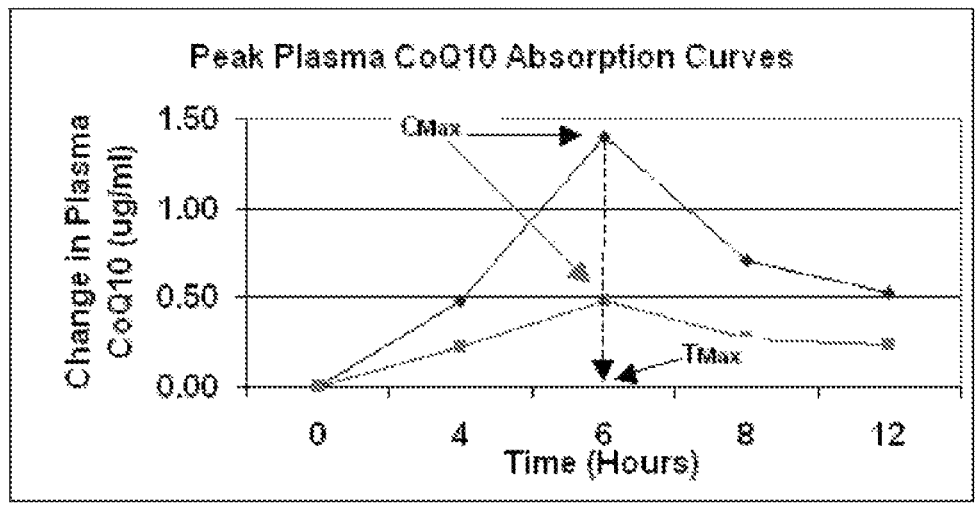
FIG. 3 provides a graphical representation of single dose peak absorption curves for the solubilized coenzyme Q-10 (60 mg) (upper line, ♦)(Example 5) formulation and Example 6 (30 mg) (lower line, ■). The Cmax for both formulations occurred at 6 hours. The change in plasma coenzyme Q-10 at Cmax was significantly greater for the solubilized coenzyme Q-10 by a three fold factor. The calculated percentage of dose absorbed at Cmax was 7.95 percent for the solubilized coenzyme Q-10 as compared to 6.04 percent for Example 6.

Peak absorption and steady state bioavailability data were compared between the solubilized $CoQ_{10}$ (Example 5) and Example 6. Comparisons were made by examining FIGS. 3 and 4. These Figures show the peak absorption curves (FIG. 3) and the steady state bioavailability curves (FIG. 4) characteristics of both the solubilized $CoQ_{10}$ and $CoQ_{10sol}$ products plotted on the same time base. Cmax for Example 6 with a 30 mg dose increased 0.53±0.28 µg/ml above the control level. With this change in plasma $CoQ_{10}$ 1813.33±96.65 µg of $CoQ_{10}$ was added to the blood at Cmax. The calculated percent (%) of ingested dose absorbed was 6.04±0.32%. This is significantly less than the 1.48±0.39 ug/ml change in plasma $CoQ_{10}$ and the 7.95±1.38% of the 60 mg ingested dose of the solubilized $CoQ_{10}$ formulation. Thus, the relative increases in the peak plasma $CoQ_{10}$ at Cmax, the amount of $CoQ_{10}$ absorbed at Cmax and the percent of ingested dose absorbed at Cmax between the solubilized $CoQ_{10}$ (Example 5) and Example 6 formulations were 80, 60 and 40 percent greater respectively for the solubilized $CoQ_{10}$ formulation. These data show that Example 6 at a dose of 30 mg is significantly (p<0.01) less absorbed than 60 mg of solubilized $CoQ_{10}$ formulation. The steady state bioavailability of Example 6 is also significantly less than that of solubilized $CoQ_{10}$ formulation as shown in FIG. 4.

At 28 days with a 60 mg daily dose, Example 6 resulted in a group mean steady state plasma $CoQ_{10}$ level of 2.26±0.74 µg/ml. This is significantly (p≤0.01) less than the 2.75±0.22 µg/ml measured for the solubilized $CoQ_{10}$ formulation using the same 60 mg/day dose. Similarly, the AUCo-28 day for the solubilized $CoQ_{10}$, $CoQ_{10}$ was significantly greater (p≤0.01) than that found for Example 6 (42.27±2.29-vs.-29.6±4.61 µg/ml/day). These data comparisons also show that the solubilized $CoQ_{10}$ formulation $CoQ_{10}$ bioavailability is significantly greater than that of Example 6.

Not to be limited by theory, as to why the solubilized $CoQ_{10}$ formulation (Example 5) has better absorption than Example 6 may be explained by the physical characteristics of the two formulations. Both Example 6 and the solubilized $CoQ_{10}$ formulations were made by the same soft gel encapsulating process. The ingredients in the two formulations were different relative to the lipid carrier molecules (Rice bran oil in Example 6 and Soybean oil and D-Limonene oil in the solubilized $CoQ_{10}$ formulation (Example 5)). On examination of the two formulations, the contents of both were an oily matrix. The solubilized $CoQ_{10}$ formulation appeared to be more liquid (less solids) than Example 6. Example 6 was reddish brown in color due to the beta-carotene. The solubilized $CoQ_{10}$ formulation was dark brown in color. Upon microscopic examination Example 6 was found to have small crystals, whereas the solubilized $CoQ_{10}$ was devoid of crystals. It is postulated that the solubilized $CoQ_{10}$ formulation consists of a larger fraction of single $CoQ_{10}$ molecules and exerts a greater osmotic concentration of $CoQ_{10}$ outside the intestinal cells, thus a greater driving force for the facilitated diffusion process for $CoQ_{10}$ absorption.

Since the $CoQ_{10}$ crystal has a melting point 10° centigrade above body temperature (37° C.) and completely melt to single molecules at 65° centigrade, it is believed that the lower absorption of Example 6 is due to the larger proportion of $CoQ_{10}$ crystals in solution and the physiological fact that the body cannot absorb a crystal. Only single molecules in water or lipid solution can be absorbed across the intestinal mucosal membrane or transported across any epithelial cell membrane.

In summary, the solubilized $CoQ_{10}$ formulation peak absorption kinetics and steady state bioavailability is significantly greater than that of Example 6. The 7.95% absorption of the ingested dose makes this a superior composition to provide increased amounts of $CoQ_{10}$ to a subject in need thereof.

Although the present invention has been described with reference to preferred embodiments, persons skilled in the art will recognize that changes may be made in form and detail without departing from the spirit and scope of the invention.

All literature and patent references cited throughout the application are incorporated by reference into the application for all purposes.

What is claimed is:

1. A solubilized composition comprising:
    a) coenzyme Q-10 or an analog thereof;
    b) a sufficient quantity of d-limonene or a derivative thereof suitable to solubilize said coenzyme Q-10 or analog thereof and keep it solubilized at ambient temperature: and
    c) an acceptable carrier, wherein between about 5 percent and about 12 percent of the coenzyme Q-10 in said composition is absorbed into the blood stream of a healthy human.

2. The composition of claim 1, wherein said coenzyme Q-10 or an analog thereof is selected from the group consisting of coenzyme Q-10, reduced coenzyme Q-10 and semi-reduced coenzyme Q-10.

3. The composition of claim 1, wherein said limonene derivative is selected from the group consisting of perillyl alcohol, perillic acid, cis-dihydroperillic acid, trans-dihydroperillic acid, a methyl ester of perillic acid, a methyl ester of dihydroperillic acid, limonene-2-diol, uroterpenol, and a combination thereof.

4. The composition of claim 1, wherein said composition is in the form of a solution, an elixir, a suspension, or a capsule.

5. The composition of claim 4, wherein said capsule is a soft gelatin capsule.

6. The composition of claim 5, wherein said carrier is soybean oil.

7. A solubilized coenzyme Q-10 composition comprising:
    a) coenzyme Q-10 or an analog thereof;
    b) a sufficient quantity of d-limonene or a derivative thereof suitable to solubilize said coenzyme Q-10 or analog thereof; and
    c) an acceptable carrier, wherein said composition provides a steady state plasma level concentration of between about 2.5 µg/ml to about 3.5 µg/ml of coenzyme Q-10 or analog thereof.

8. The composition of claim 7, wherein said coenzyme Q-10 or an analog thereof is selected from the group consisting of coenzyme Q-10, reduced coenzyme Q-10 and semi-reduced coenzyme Q-10.

9. The composition of claim 7, wherein said limonene derivative is selected from the group consisting of perillyl alcohol, perillic acid, cis-dihydroperillic acid, trans-dihydroperillic acid, a methyl ester of perillic acid, a methyl ester of dihydroperillic acid, limonene-2-diol, uroterpenol, and a combination thereof.

10. The composition of claim 7, wherein said composition is in the form of a solution, an elixir, a suspension, or a capsule.

11. The composition of claim 10, wherein said capsule is a soft gelatin capsule.

12. The composition of claim 11, wherein said carrier is soybean oil.

13. A solubilized coenzyme Q-10 composition comprising:
   a) coenzyme Q-10 or an analog thereof;
   b) a sufficient quantity of d-limonene or a derivative thereof suitable to solubilize said coenzyme Q-10 or analog thereof; and
   c) an acceptable carrier, wherein said composition provides a peak plasma level of between about 2.1 µg/ml to about 3.0 µg/ml of coenzyme Q-10 or analog thereof.

14. The composition of claim 13, wherein said coenzyme Q-10 or an analog thereof is selected from the group consisting of coenzyme Q-10, reduced coenzyme Q-10 and semi-reduced coenzyme Q-10.

15. The composition of claim 13, wherein said limonene derivative is selected from the group consisting of perillyl alcohol, perillic acid, cis-dihydroperillic acid, trans-dihydroperillic acid, a methyl ester of perillic acid, a methyl ester of dihydroperillic acid, limonene-2-diol, uroterpenol, and a combination thereof.

16. The composition of claim 13, wherein said composition is in the form of a solution, an elixir, a suspension, or a capsule.

17. The composition of claim 16, wherein said capsule is a soft gelatin capsule.

18. The composition of claim 1, wherein the composition further includes an additional antioxidant.

19. The composition of claim 18, wherein the additional antioxidant is tocopherol.

* * * * *